United States Patent [19]

Ojima et al.

[11] 4,351,318
[45] Sep. 28, 1982

[54] POCKET BODY WARMER WITH A CIGARETTE LIGHTER

[75] Inventors: Shin Ojima, Yao; Yoshiaki Neriki, Nara, both of Japan

[73] Assignee: Hosiden Electronics Co., Ltd., Osaka, Japan

[21] Appl. No.: 158,027

[22] Filed: Jun. 9, 1980

[51] Int. Cl.³ .................. A61F 7/08; F23Q 1/02; F23D 3/18; F23D 3/40

[52] U.S. Cl. ...................... 126/208; 431/277; 431/274; 431/312; 431/324; 431/326; 431/344; 131/178

[58] Field of Search .......... 431/253, 268, 277, 274, 431/312, 324, 323, 320, 344, 326; 126/208, 209, 96; 131/178, 225; 206/86, 87

[56] References Cited

U.S. PATENT DOCUMENTS

| | | | |
|---|---|---|---|
| 2,433,707 | 12/1947 | Phillips | 431/277 X |
| 2,670,728 | 3/1954 | Smith | 126/208 |
| 2,814,190 | 11/1957 | Bryant | 431/277 |
| 2,914,060 | 11/1959 | Wilcox | 126/208 |
| 2,986,027 | 5/1961 | Lockwood | 431/277 X |
| 3,295,510 | 1/1967 | Matoba | 126/208 |
| 3,723,048 | 3/1973 | Russell | 431/277 X |
| 3,966,392 | 6/1976 | Lockwood | 431/277 X |

Primary Examiner—Samuel Scott
Assistant Examiner—Randall L. Green
Attorney, Agent, or Firm—Pollock, Vande Sande & Priddy

[57] ABSTRACT

On one end face of a case, a heating unit, a burner and a firing portion are aligned in this order, and a tubular windshield is mounted on the end face of the case to surround substantially entirely the burner. The windshield has formed therein an opening on the side of the heating unit, through which a lighter flame emitted from the burner is directed to the heating unit to set it alight when the case is turned down so that the heating unit lies above the burner.

5 Claims, 9 Drawing Figures

POCKET BODY WARMER WITH A CIGARETTE LIGHTER

BACKGROUND OF THE INVENTION

This invention relates to a pocket body warmer which is designed to be usable as a cigarette lighter, too.

Heretofore, a pocket body warmer and a cigarette lighter have been produced and sold as entirely different goods. While in use, the pocket body warmer is carried in one's pocket to warm the body, and the cigarette lighter is also carried in one's pocket and taken out of the pocket to light a cigarette or the like. The pocket body warmer and the cigarette lighter are common in that they are both carried in one's pocket for use. From this point of view, there has been proposed a pocket body warmer with a cigarette lighter incorporated therein. This conventional pocket body warmer with a cigarette lighter does not properly set the heating unit of the warmer alight by flames of the cigarette lighter. Namely, in the conventional pocket body warmer with a cigarette lighter, when the warmer is placed in position so that the flame of the lighter may reach the heating unit for setting it alight, sooty smoke is produced to cover the heating unit with soot. As a result of this, the catalytic action of a heating catalyst, which is usually platinized asbestos, is lost; namely, the function of the pocket body warmer is lowered or lost and its service life is shortened.

There has also been proposed another type of pocket body warmer with a cigarette lighter which is designed so that its lighter unit can be disassembled from the warmer case for easy replacement of a flint. In this pocket body warmer with a cigarette lighter, however, since the whole body of the lighter unit is disassembled from the case, it is difficult for fuel of the warmer to soak into a wick, and hence the lighter is slow to catch fire.

It is an object of the present invention to provide a pocket body warmer with a cigarette lighter which is adapted to be capable of setting its heating unit alight by the lighter but without lowering the function of the pocket body warmer.

Another object of the present invention is to provide a pocket body warmer with a cigarette lighter which is easy of assembling, adjusting and maintenance and is designed so that the lighter is quick to catch fire.

Still another object of the present invention is to provide a pocket body warmer with a cigarette lighter which is designed so that when it is used as a cigarette lighter, the heating unit of the warmer is prevented from firing.

SUMMARY OF THE INVENTION

According to the present invention, a heating unit of the pocket body warmer, a burner and a lighter firing portion are arranged in alignment in this order on one end face of a case. The case contains a liquid fuel for the pocket body warmer and the cigarette lighter, such as benzine, and an impregnant for soaking the fuel, such as surgical cotton. In the heating unit of the body warmer is housed platinized asbestos used as a heating catalyst, which closes an opening for volatilizing the fuel in the case, as in the conventional pocket body warmer. A tubular windshield is mounted on the abovesaid end face of the case in a manner to surround the burner. The windshield has small ventilating holes distributed therein over the entire area thereof, a much larger first opening formed on the side of the heating unit facing the heating unit for guiding thereto the flame of the lighter, and a second opening formed on the side of the lighter firing portion for permitting sparks therefrom to reach a wick of the burner. With this arrangement, after striking the lighter, when the case is turned sideways so that the heating unit lies above the burner, the flame of the lighter passes through the large first opening of the windshield to set the heating unit alight. In this case, the windshield ensures that the flame of the lighter centers on the heating unit without spreading out and the flame burns sufficiently to ignite the heating unit without producing sooty smoke. Accordingly, even if set alight by the lighter, the heating unit is not degraded by soot. On top of that, the presence of the windshield assures that, for example, when the lighter is used in conventional fashion to light a cigarette, the heating unit will not be ignited by the flame of the lighter.

Further, the lighter firing portion and the windshield are formed as a unitary structure, which is mounted on the case in a manner to be easily dismountable therefrom. In this case, the burner is fixedly attached to the case. With this arrangement, a wick is used as the burner and the wick is housed in the case, with its one end portion projecting out of the case. The wick is held in contact with the fuel impregnant in the case to draw up the fuel to be burned in the projecting end portion of the wick. In the case where the wick and the firing portion are formed as a unitary structure demountable from the case, it is difficult to attach again the structure to the case; however, where only the firing portion and the windshield are assembled together in a unit which is separate from the wick, the assembly can be easily mounted on and demounted from the case.

Further, in the case where the wick and the firing portion are together in a single unit and the wick is inserted, for example, into a tube for easy mounting and demounting, the fuel in the impregnant is not smoothly drawn up into the wick, resulting in the wick burning poorly.

In the case of forming the firing portion and the windshield as a unitary structure separate from the wick, the windshield is mounted on an auxiliary plate, a pair of opposing support pieces are formed integrally with the windshield to extend from marginal edges on both sides of the windshield opening facing the firing portion, and the shaft of a rubbing member for firing use, i.e., a spark wheel, is rotatably supported between the pair of support pieces. A tube is fixedly inserted into a hole made in the auxiliary plate. One end of the tube is disposed opposite to the peripheral surface of the rubbing member, a flint and a coiled spring are inserted into the tube from the other end thereof, and a screw is screwed into the other end of the tube to urge one end face of the flint against the peripheral surface of the rubbing member or spark wheel. The auxiliary plate is fixed in contact with the end face of the case and, in this case, the tube is inserted into the case through a hole made therein. The auxiliary plate has another hole, through which the wick housed in and attached to the case projects outwardly into the windshield. One end of the auxiliary plate is fitted under a lug formed in the end face of the case and the other end of the plate is fixed by a screw to the case. By simply unscrewing the screw, the unitary structure of the firing portion and the windshield can easily be disassembled from the case while the wick remains attached to the case. With this unitary structure removed, replacement of the flint and adjustment of the pressure of the flint to the rubbing member can easily be performed. The operation of attaching the unitary structure again to the case is also easy. In order to carry out the replacement of the flint and adjustment of its pressure in the state that the firing portion is fixed to the case, the tube must be lengthened and working of a replacement-adjustment portion provided on the outside of the case is cumbersome for it is necessary to construct this portion in a manner to prevent leakage of the fuel.

DESCRIPTION OF THE PREFERRED EMBODIMENTS

Figure 1:
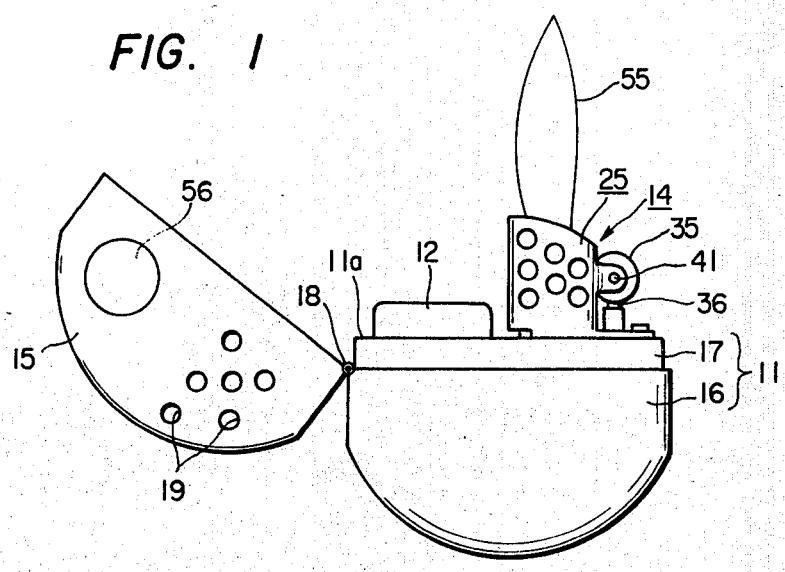
FIG. 1 is a front view showing one example of the pocket body warmer with a cigarette lighter according to the present invention, with its lid open.
Figure 2:
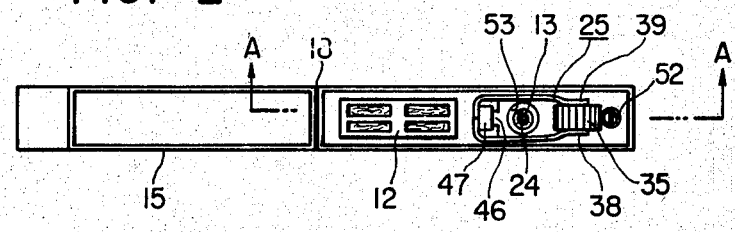
FIG. 2 is a plan view of FIG. 1.
Figure 3:
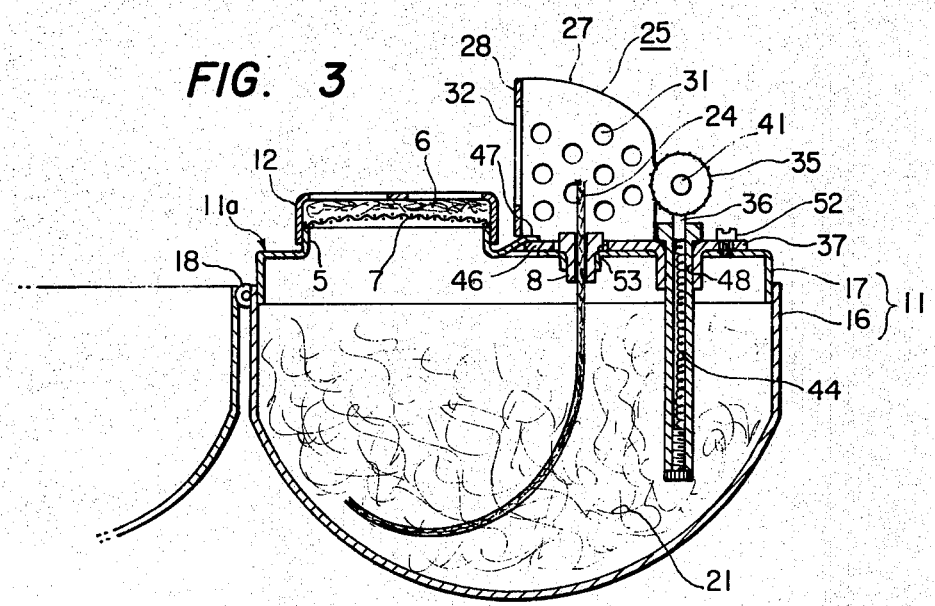
FIG. 3 is a sectional view taken on the line A—A in FIG. 2.
Figure 4:
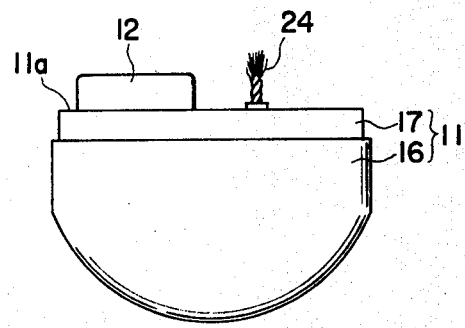
FIG. 4 is a front view of the pocket body warmer with a cigarette lighter of FIG. 1, with a lid 15, a firing portion 14 and a windshield removed.

As illustrated in FIGS. 1 to 3, the invention comprises a thin metal case 11, one end of which is rounded, and the other end face 11a is formed flat, on which are arranged in its lengthwise direction a heating unit 12, a flame forming portion 13 and a firing portion 14. A lid 15 is pivotally mounted at one end of the case 11 to cover the heating unit 12, the flame forming portion 13 and the firing portion 14. The case 11 comprises a case body 16 and an engaging portion 17 for engagement with the lid 15. The case body 16 is open at one end face, into which the engaging portion 17 is fitted with its upper portion projecting out therefrom. The engaging portion 17 is soldered to the case body 16 so that fuel in the case 11 may not leak out therefrom. When put on the case 11, the lid 15 snugly receives the engaging portion 17. In the illustrated example, the lid 15 is hinged to the marginal edge of the case body 16 on the side of the engaging portion 17 at one end in its lengthwise direction, as indicated by 18; namely, the lid 15 is pivotal about the hinge 18 to cover and uncover the case 11. The lid 15 is also formed of thin metal as is the case 11, and is rounded at both ends on the opposite side from the case 11. Ventilating holes 19 are formed in both side walls of that portion of the lid 15 which lie adjacent to the heating unit 12 when the lid 15 is in its closed position on the case 11.

The case 11 is filled with a fuel impregnant 21, such as surgical cotton, for soaking fuel. The heating unit 12 is positioned on the side of end face 11a adjacent the hinge 18 and is snugly fitted into a marginal projection of a fuel volatilizing opening 5, formed in the end face 11a of the case 11, in a manner to cover the opening 5. The heating unit 12 has housed therein platinized asbestos 6 which is a heating catalyst, the platinized asbestos 6 being retained in place by a wire net 7. The heating unit 12 can be disassembled from the case 11 and the fuel, for example, benzine can then be poured into the case 11 through the opening 5. The heating unit 12 and the structure for attaching it to the case 11 are the same as in the prior art.

The burner 13 is formed by a wick 24, which is inserted into a sleeve 8 and retained by it. The sleeve 8 is forced into a hole made in the end face 11a of the case 11. One end portion of the wick 24 projects out of the case 11 and the other end portion is held in contact with the fuel impregnant 21 to draw up therefrom the fuel to the projecting end portion of the wick 24. The wick 24 is, for example, a braid of asbestos and glass fiber which is capable of soaking and drawing up the fuel. The wick 24 may be the same as those used in ordinary cigarette lighters. When set alight, the wick 24 produces a flame.

Figure 7:
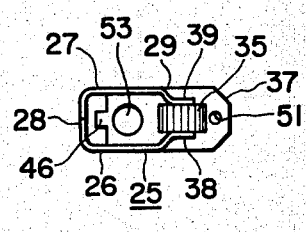
FIG. 7 is a plan view of FIG. 6.
Figure 8:
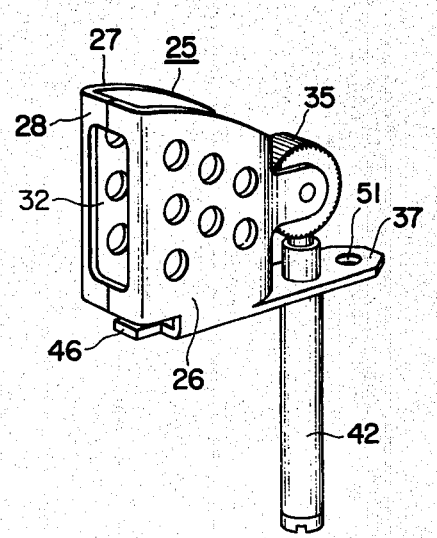
FIG. 8 is a perspective view of FIG. 6.

A tubular windshield 25 is mounted on the end face 11a of the case 11 to substantially encompass the flame forming portion 13. The windshield 25 is composed of, for example, panels 26 and 27 (see FIGS. 7 and 8) extending along both sides of the lid 15, a panel 28 interconnecting the panels 26 and 27 on the side of the heating unit 12 and a panel 29 interconnecting the panels 26 and 27 on the side of the firing portion 14. The panels 26 and 27 have distributed therein small holes 31. An opening 32, much larger than the openings 31 as shown in FIG. 8, is formed in the windshield 25 on the side of the heating unit 12, that is, in the panel 28, through which the flame of the lighter formed in the windshield 25 can be guided to the heating unit 12. Also in the windshield 25 on the side of the firing portion 14, that is, in the panel 29 is opened to the outside to form another opening, through which sparks from the firing portion 14 can be directed to the wick 24. The wick 24 is disposed in the windshield 25 substantially centrally thereof.

Figure 6:
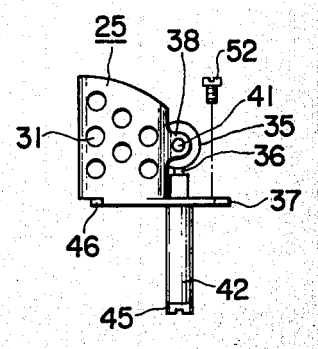
FIG. 6 is a front view showing the firing portion and the windshield disassembled from the pocket body warmer.

The firing portion 14 and the windshield 25 are formed as a unitary structure, which is arranged to be assembled with or disassembled from the case 11 relatively easily. In the firing portion 14, a flint 36 is urged against a rubbing member or spark wheel 35 so that sparks may be generated by rubbing the peripheral surface of the rubbing member 35 against the flint 36. To this end, for example, the following structure is adopted. As illustrated in FIGS. 6 to 8, an auxiliary plate 37 is provided and its marginal portions are bent substantially at right angles to form the pair of opposing panels 26 and 27. The panels 26 and 27 are bent inwardly at one marginal portion so that they are contiguous to each other to form the panel 28. The other marginal portions of the panels 26 and 27 are also bent inwardly to form the panel 29 and the bent portions partly extend substantially in parallel with the panels 26 and 27 on the opposite side from the panel 28 to form a pair of opposing support pieces 38 and 39. Between the support pieces 38 and 39 is disposed a thick, disc-shaped rubbing member 35, whose shaft 41 is inserted at both ends into holes made in the support pieces 38 and 39 to rotatably support therebetween the rubbing member 35. The periphery of the rubbing member 35 forms a striking surface.

Figure 5:
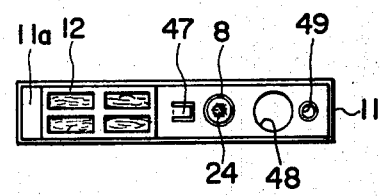
FIG. 5 is a plan of FIG. 4.

The auxiliary plate 37 has a hole opposite the rubbing member 35, and a tube 42 is inserted into this hole and fixed therein. One end face of the tube 42 is disposed in adjacent but spaced relation to the striking surface of the rubbing member 35. A flint 36 and a coiled spring are inserted into the tube 42 from the other end thereof, and a screw 45 is screwed into engagement with a female screw cut in the inner surface of the other end portion of the tube 42, pressing one end face of the flint against the periphery of the rubbing member 35. The auxiliary plate 37 is demountably mounted on the end face 11a of the case 11. A small projection 46 is formed integrally with the auxiliary plate 37 to extend from the center of its marginal edge on the side of the windshield 25. Between the heating unit 12 and the wick 24 therein is formed in the end face 11a a lug 47 which extends slightly upwards from the side of the wick 24 to provide a small gap for receiving the small projection 46, as shown in FIGS. 3 and 5. In the end face 11a of the case 11 there are made a round hole 48 for receiving the tube 42 and a threaded hole 49 positioned on the opposite side from the wick 24 with respect to the round hole 48. The small projection 46 of the auxiliary plate 37 is inserted below the lug 47; the tube 42 is inserted into the case 11 through the round hole 48; the auxiliary plate 37 is placed in contact with the end face 11a of the case 11; and, in this state, a screw 52 is screwed into the threaded hole 49 through a hole 51 made in the auxiliary plate 37 at the position corresponding to the threaded hole 49, thereby clamping the auxiliary plate 37 to the case 11. The auxiliary plate 37 has an opening 53 for receiving the wick 24.

As shown in FIG. 1, a piece of cloth 56 is attached to the outside of each of the side plates of the lid 15 on the side opposite from the hinge 18. The lid 15 becomes appreciably hot by the heat of the heating unit, but when it is desired to use the lighter, the lid 15 can be lifted by holding it between one's fingers at the cloth portions 56.

Figure 9:
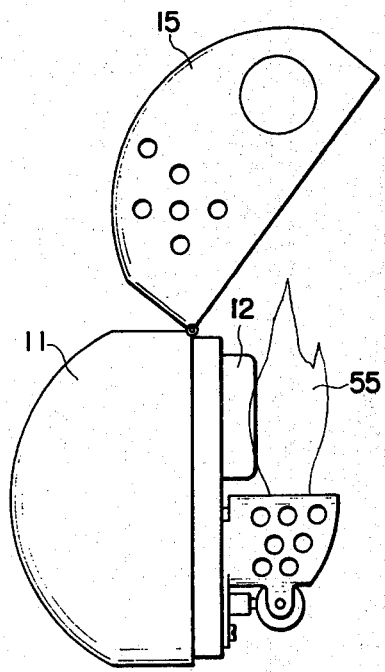
FIG. 9 is a front view of the pocket body warmer with a cigarette lighter of this invention in the state in which the heating unit of the body warmer is being set alight.

When the pocket body warmer with the cigarette lighter, constructed as described above, is put to use, the heating unit 12 is first disassembled from the case 11, and fuel is poured into the case 11, and then the heating unit 12 is mounted again on the case 11, as described previously. In the case of using the lighter in the above state, the rubbing member 35 is driven clockwise in FIG. 1 to produce sparks by friction with the flint 36. The sparks reach the wick 24 through the opening between the panels 26 and 27 to set the wick 24 alight to emit therefrom a flame 55 for the fuel previously poured into the case 11 is drawn up to the top end portion of the wick 24. When it is desired to use the pocket body warmer, the case 11 is turned substantially 90° from its upright cigarette lighter orientation so that the heating unit may lie above the windshield 25, as shown in FIG. 9, after striking the lighter. When the case is so turned, the flame 55 passes through the large opening 32 of the windshield 25 which faces the heating unit 12, heating the platinized asbestos 6 housed therein. When the heating unit 12 is heated sufficiently, the fuel volatilized from the case 11 catches fire and continues burning. By putting the lid 15 on the case 11, the flame 55 is extinguished, but in the heating unit 12, the fuel is gradually volatilized and continues burning to maintain high temperature. The production of the flame 55 and the burning in the heating unit 12 are respectively carried out by the same actions as in the cigarette lighter and the pocket body warmer heretofore employed.

In the pocket body warmer with the cigarette lighter according to the present invention, the heating unit 12 can be ignited by the lighter action, as described above. In this case, the presence of the windshield 25 ensures a smooth air flow therein through the opening 32 and the air holes 31, and the windshield 25 itself is also heated to facilitate the evaporation of the fuel, so that the fuel is sufficiently burnt in the flame 55 and no sooty flame is emitted. It has been found that use of the windshield 25 is necessary to proper ignition and operation of the heating unit since, when the heating unit 12 is ignited by the lighter flame with the windshield 25 removed, the flame becomes very sooty, resulting in the heating unit 12 being stained with soot. Since the firing portion 13 and the heating unit 12 are adjacent to each other, the central portion rather than the tip portion of lighter flame 55 contacts the heating portion 12, and even if the flame 55 becomes sooty at its tip end, the heating unit 12 is not stained with soot. The pocket body warmer with the cigarette lighter according to the present invention is very convenient in that the heating unit 12 can be set alight by the lighter in the way described above. On top of that, since no sooty flame is produced, the operation of heating unit 12 is not degraded and is long-lived. The windshield 25 serves to center the flame 55 on the heating unit 12 without spreading it to provide for enhanced efficiency in igniting the heating unit 12.

Moreover, the firing portion 14 and the windshield 25 are formed as a unitary structure, which is removable from the case 11, so that replacement of the flint 36 and adjustment of the pressure for urging the flint 36 against the rubbing member 35 can be easily carried out. Besides, according to the foregoing embodiment, the firing portion 14 can be disassembled from the case 11 by simply unscrewing the screw 52 and it can be fixed again to the case 11 by simply tightening the screw 52 into place; namely, the firing portion 14 can be assembled with and disassembled from the case 11 with much ease. It is also possible to extend the tube 42 to project out from the case 11 on the side opposite from its end face 11a so that replacement of the flint and adjustment of the pressure of the flint to the rubbing member may be performed without removing the firing portion 14. In this case, however, special steps are required for preventing leakage of the fuel from the projecting end portion of the tube 42 on the side of the screw 45. The pocket body warmer with the cigarette lighter according to the present invention can easily be produced without involving such troublesome working. In the case where the lighter unit including the burner is arranged to be disassembled from the case 11, the operation of mounting the lighter unit on the case 11 is difficult since the wick 24 is long enough to make direct contact with the fuel impregnant 21. In the present invention, however, the wick 24 is fixed to the case 11 and only the firing portion and the windshield are arranged to be removable from the case, so that their mounting and demounting operation is simple and easy.

In the case where the wick 24 and the firing portion 14 are housed in a tubular member so that the entire lighter unit may be disassembled from the case 11, the fuel in the impregnant 21 does not smoothly soak in the wick 24, resulting in the wick 24 becoming slow to catch fire. Especially in the case where the lighter unit is disassembled from the case for replacement of the flint or adjustment of the pressure of the flint to the rubbing member, an appreciable amount of time is required for the fuel to be drawn up to the projecting end of the wick 24 after mounting again the lighter unit on the case. In the present invention, however, since the wick 24 is not disassembled from the case, the fuel is always supplied to the projecting end of the wick; accordingly, the wick can be kindled immediately after replacement of the flint with a new one. In the present invention, the heating unit 12 and the burner 13 are disposed in close proximity, but the windshield 25 prevents the heating unit 12 from being set alight by the lighter flame 55 when the lighter is used only to light a cigarette or for some other purposes. Since the heating unit 12 and the burner 13 can be disposed close to each other, the heating unit 12 is not heated directly by the lip of the flame 55 when set alight by the flame 55, and consequently, the heating unit 12 is not stained with soot.

It will be apparent that many modifications and variations may be effected without departing from the scope of the novel concepts of this invention.

What is claimed is:

1. A pocket body warmer with an integrated cigarette lighter, comprising:
    a case for containing a liquid fuel;
    a fuel impregnant housed in the case for soaking up the liquid fuel poured into the case;
    a heating unit mounted on one end face of the case, said heating unit covering an opening formed in said end face and having housed therein a platinized catalyst for burning evaporated fuel to generate heat;
    a burner located on said end face of said case adjacent said heating unit, said burner comprising a wick mounted on said case and having one end portion which projects outwardly from said end face of the case and an opposite end portion which is inserted into the case to extend into contact with the fuel impregnant to draw up therefrom the fuel, the projecting end portion of said wick being adapted to be ignited to emit a lighter flame;
    a firing structure located on said end face of said case, on the opposite side of said end face from the heating unit with respect to the wick, for generating sparks to ignite said wick;
    a substantially tubular windshield located on said end face of the case in surrounding relation to said wick, said windshield having a plurality of small air holes therein, said windshield also defining a first opening having a size larger than that of any of said air holes and located on the side of said windshield facing said heater unit for selectively directing the lighter flame produced by said burner toward said heating unit when said case is turned through an angle such that said heating unit is located above said windshield, and said windshield also defining a second opening on the side of said windshield opposite to said first opening and facing said firing structure for directing the sparks from the firing structure to the wick; and
    a lid for removably covering the heating unit, the burner, the firing structure and the windshield;
    said firing structure and windshield being integrated with one another in a unitary assembly which is attached as a unit to said end face of said case, said unitary assembly being adapted to be detached as a unit from said end face of said case and removed from the vicinity of said wick with said wick remaining mounted on said case.

2. A pocket body warmer with a cigarette lighter according to claim 1, wherein said unitary assembly comprises an auxiliary plate of metal which is demountably attached by mounting means to said end face of the case; the windshield being integral with said auxiliary plate and being formed by bent marginal portions of said auxiliary plate; a pair of opposing support pieces integral with said auxiliary plate and formed to extend towards said firing structure from the marginal edges of said second opening of the windshield; said firing structure comprising a rubbing member which is mounted for rotation on a shaft extending between the pair of support pieces; a tube fixedly inserted into a hole in said auxiliary plate in alignment with the rubbing member; one end of said tube being inserted into said case through a hole made in said end face of the case; the other end of said tube being disposed adjacent to the peripheral surface of said rubbing member; a flint housed in said tube at its said other end; a screw member in thread engagement with said one end of said tube; a coiled spring in said tube interposed between said screw member and the flint for urging the flint against the peripheral surface of said rubbing member; and a hole in the auxiliary plate through which said wick may pass, said wick being attached to the case and being separate from said unitary assembly whereby said unitary assembly may be detached from said case while said wick remains attached to said case.

3. A pocket body warmer with a cigarette lighter according to claim 2 wherein said mounting means comprises means on said end face of the case for separately engaging one end portion of the auxiliary plate, and means for screw attaching the other end portion of the auxiliary plate to the case.

4. The body warmer and cigarette lighter of claim 1 wherein said unitary assembly comprises an elongated auxiliary plate dimensioned to overlie said end face of said case, said windshield being integral with and upstanding from said auxiliary plate, said firing structure including a spark wheel which is mounted for rotation between a pair of support arms that are integral with said plate and windshield, and mounting means on said end face of said case for detachably affixing said auxiliary plate to said end face of said case.

5. The body warmer and cigarette lighter of claim 4 wherein said mounting means comprises a lug on said end face of said case, one end of said elongated auxiliary plate being adapted to separably engage said lug, and a screw member for threadably attaching the other end of said plate to said end face of said case.

* * * * *